(12) United States Patent
Ramos et al.

(10) Patent No.: US 11,001,544 B2
(45) Date of Patent: May 11, 2021

(54) TRANSALKYATION PROCESSES IN THE PRESENCE OF SULFOLANE

(71) Applicant: ExxonMobil Chemical Patents Inc., Baytown, TX (US)

(72) Inventors: Jesus A. Ramos, Houston, TX (US); Robert G. Tinger, Friendswood, TX (US); Paul Podsiadlo, Humble, TX (US); Todd E. Detjen, Houston, TX (US); Kathleen M. Keville, Beaumont, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/930,215

(22) Filed: May 12, 2020

(65) Prior Publication Data

US 2020/0407291 A1    Dec. 31, 2020

Related U.S. Application Data

(60) Provisional application No. 62/868,507, filed on Jun. 28, 2019.

(51) Int. Cl.
*C07C 6/12* (2006.01)

(52) U.S. Cl.
CPC .................................. *C07C 6/126* (2013.01)

(58) Field of Classification Search
None
See application file for complete search history.

(56) References Cited

U.S. PATENT DOCUMENTS

| 3,953,324 | A | * | 4/1976 | Deal | C10G 21/28 208/321 |
| 5,952,536 | A |   | 9/1999 | Nacamuli et al. | |
| 2011/0190560 | A1 | * | 8/2011 | Cao | C07C 2/66 585/467 |
| 2015/0141700 | A1 |   | 5/2015 | Johnson et al. | |
| 2016/0220987 | A1 |   | 8/2016 | Lai et al. | |
| 2018/0223197 | A1 | * | 8/2018 | Al-Ghamdi | C10G 47/00 |

* cited by examiner

*Primary Examiner* — Philip Y Louie

(57) ABSTRACT

Co-feeding sulfolane into a transalkylation reactor along with the aromatic hydrocarbon feed(s) can improve benzene purity of the benzene product stream produced from the transalkylation product mixture, especially at the beginning phase of a catalyst cycle.

27 Claims, 2 Drawing Sheets

TRANSALKYATION PROCESSES IN THE PRESENCE OF SULFOLANE

CROSS-REFERENCE TO RELATED APPLICATIONS

This application claims priority to and the benefit of U.S. provisional application Ser. No. 62/868,507, having a filing date of Jun. 28, 2019, the disclosure of which is incorporated herein by reference.

FIELD

This disclosure relates to transalkylation of aromatic hydrocarbons. In particular, this disclosure relates to transalkylation between C9+ aromatic hydrocarbons and C6-C7 aromatic hydrocarbons for the production of xylenes, particularly p-xylene, and benzene. This disclosure is useful, e.g., in making p-xylene and benzene from a naphtha reformate stream.

BACKGROUND

Refineries have focused on the production of benzene and xylene by transalkylation of C9+ aromatics and toluene over noble metal-containing zeolite catalysts. During the transalkylation of C9+ aromatics and toluene to higher value petrochemical products, such as benzene and xylene, over catalysts containing noble metals, by-product saturate compounds are typically produced during the first several months on stream. These by-product saturate compounds, referred to as co-boilers, can boil in the same temperature range as a high value petrochemical product, making separation of the high value petrochemical product at high purity levels difficult. Particularly with respect to the benzene product, the presence of co-boilers such as methylcyclopentane, cyclohexane, 2,3-dimethylpentane, dimethylcyclopentane and 3-methylhexane at high concentrations can significantly reduce its quality. Therefore, an additional solvent extraction step may be required in order to produce a benzene product with a high purity.

Solvent extraction of benzene adds to the complexity to the production process and increases costs to the benzene product. It would be highly desirable to have a transalkylation process in which the formation of co-boilers of C6-C7 aromatic hydrocarbons are minimized, such that a high-purity benzene product may be produced from the transalkylation effluent without the need of an intermediate solvent extraction of benzene and/or toluene.

This disclosure satisfies this and other needs.

SUMMARY

It has been found, in a surprising manner, that by introducing sulfolane (tetrahydrothiophene 1,1-dioxide,

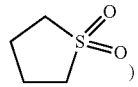

into the transalkylation reactor along with the C9+ aromatic hydrocarbon feed and the benzene/toluene feed, one can suppress the formation of co-boilers of benzene/toluene in the transalkylation reactor, such that a high-purity benzene product can be produced from the transalkylation effluent without an intermediate solvent extraction process, especially in proximity to the beginning phase of a transalkylation process. More surprisingly, where sulfolane is introduced at an appropriate amount, after ceasing the introduction, the benzene product purity improvement can be retained.

In a first aspect, this disclosure relates to a transalkylation process comprising: introducing a C9+ aromatic feed, sulfolane, molecular hydrogen ($H_2$), and at least one of benzene and toluene into a transalkylation reactor having a transalkylation catalyst disposed therein; and contacting the C9+ aromatic feed, the sulfolane, and the at least one of benzene and toluene with the transalkylation catalyst for a first period of time under transalkylation conditions to produce a product mixture.

In a second aspect, this disclosure relates to a transalkylation process comprising: feeding a C9+ aromatic feed, molecular hydrogen ($H_2$), sulfolane and at least one of benzene and toluene into a transalkylation reactor having a transalkylation catalyst comprising a metal disposed therein, where the sulfolane is fed at a quantity from 50 ppm to 400 ppm, based on the total weight of the C9+ aromatic feed, the at least one of benzene and toluene; contacting the C9+ aromatic feed, the at least one of benzene and toluene, the molecular hydrogen, and the sulfolane with the transalkylation catalyst for a first period of time under transalkylation conditions to produce a product mixture rich in xylenes, wherein the transalkylation conditions comprise a feed inlet temperature from 200° C. to 550° C., a hydrogen to hydrocarbon molar ratio from 1.5 to 10, and an absolute pressure from 380 kPa to 4240 kPa; and at the end of the first period, ceasing feeding the sulfolane to the transalkylation reactor; supplying at least a portion of the product mixture to a benzene distillation column without an intermediate solvent extraction process; and obtaining a benzene product stream from the benzene distillation column.

DETAILED DESCRIPTION

Figure 1:
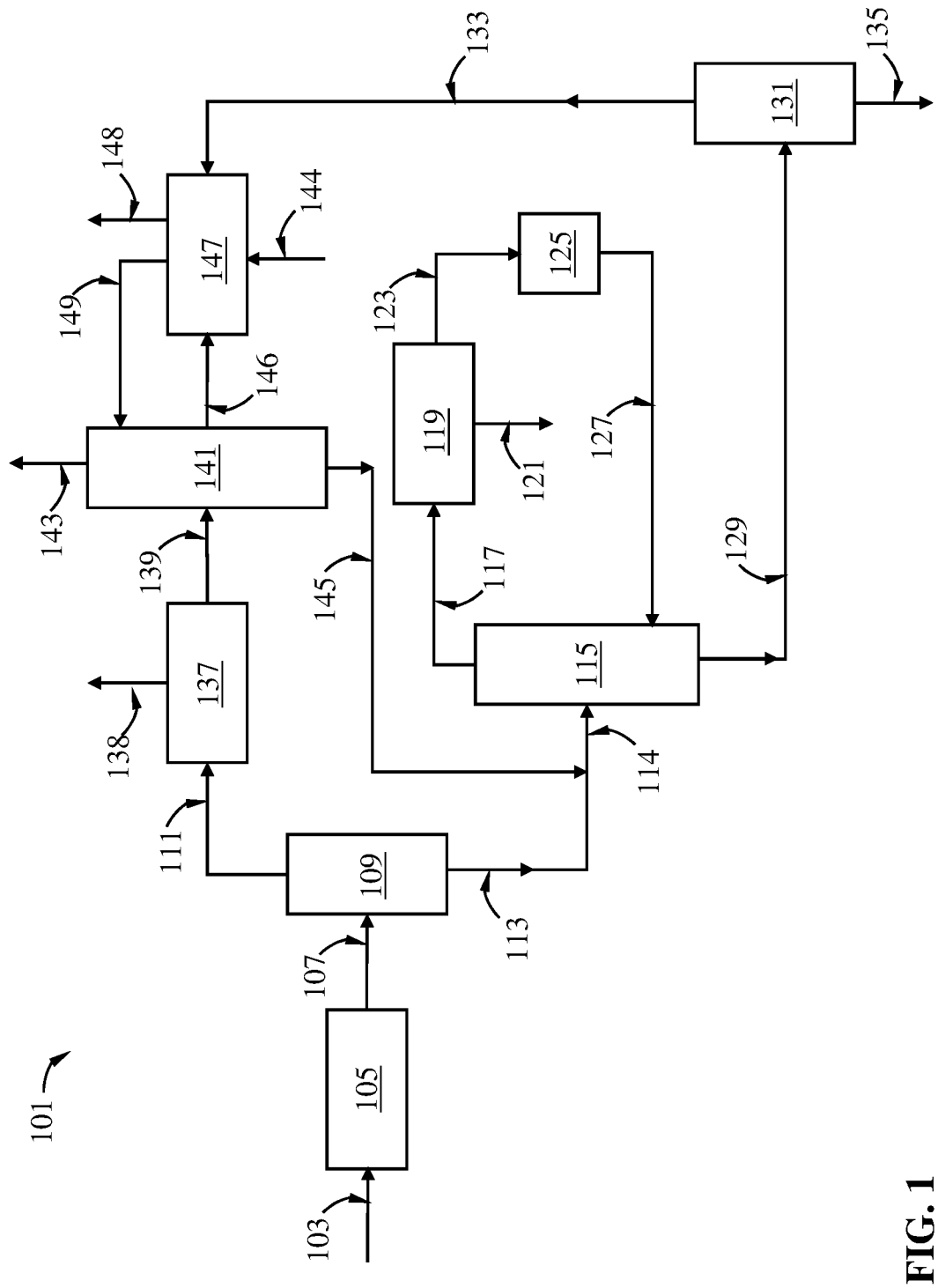
FIG. 1 schematically illustrates a process for making p-xylene and benzene from a naphtha reformate including an exemplary transalkylation process of this disclosure.

It is to be understood that the following disclosure describes several exemplary embodiments for implementing different features, structures, and/or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. Moreover, the exemplary embodiments presented below can be combined in any combination of ways, i.e., any element from one exemplary embodiment can be used in any other exemplary embodiment, without departing from the scope of the disclosure.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step(s), or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation tower" include embodiments where one, two or more fractionation columns are used, unless specified to the contrary or the context clearly indicates that only one fractionation column is used. Likewise, "a C9+ stream" should be interpreted to include one, two, or more C9+ components, unless specified or indicated by the context to mean only one specific C9+ component.

As used herein, the generic term "xylene," either in singular or plural form, shall collectively mean one of or any mixture of two or three of para-xylene, meta-xylene, and ortho-xylene at any proportion thereof. The term "mixed xylenes" means a combination of all three isomers of xylene.

As used herein, the term "rich" when used in phrases such as "X-rich" or "rich in X" means, with respect to an outgoing stream obtained from a device, that the stream comprises material X at a concentration higher than in a feed material fed to the same device from which the stream is derived.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm", as used herein, are ppm by weight unless specified otherwise. All concentrations herein are expressed on the basis of the total amount of the composition in question. Thus, e.g., the concentrations of the various components of a feed composition are expressed based on the total weight of the feed composition. All ranges expressed herein should include both end points as two specific embodiments unless specified or indicated to the contrary.

The term "aromatic" as used herein is to be understood in accordance with its art-recognized scope which includes alkyl substituted and unsubstituted mono- and polynuclear compounds.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). The term "Cn aromatic hydrocarbon," where n is a positive integer, means (i) any aromatic hydrocarbon compound comprising carbon atom(s) in its molecule at the total number of n, or (ii) any mixture of two or more such aromatic hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cm to Cn aromatic hydrocarbon" or "Cm-Cn hydrocarbon," where m and n are positive integers and m<n, means any of Cm, Cm+1, Cm+2, . . . , Cn−1, Cn aromatic hydrocarbons, or any mixtures of two or more thereof. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s). A "Cn+ aromatic hydrocarbon" means (i) any aromatic hydrocarbon compound comprising carbon atom(s) in its molecule at the total number of at least n, or (ii) any mixture of two or more such aromatic hydrocarbon compounds in (i). A "Cn− aromatic hydrocarbon" means (i) any aromatic hydrocarbon compound comprising carbon atoms in its molecule at the total number of at most n, or (ii) any mixture of two or more such aromatic hydrocarbon compounds in (i). A "Cm aromatic hydrocarbon stream" means a hydrocarbon stream consisting essentially of Cm aromatic hydrocarbon(s). A "Cm-Cn aromatic hydrocarbon stream" means a hydrocarbon stream consisting essentially of Cm-Cn aromatic hydrocarbon(s).

The term "rich" when describing a component in a stream means that the stream comprises the component at a quantity higher than a source material from which the stream is derived. The term "depleted" when describing a component in a stream means that the stream comprises the component at a quantity lower than a source material from which the stream is derived. Thus, in an embodiment where a C8 aromatic hydrocarbon feed stream consisting essentially of the xylenes and ethylbenzene is fed into a p-xylene recovery sub-system such as a crystallizer to obtain a p-xylene product stream comprising p-xylene at a concentration higher than the C8 aromatic hydrocarbon feed stream and ethylbenzene at a concentration lower than the C8 aromatic feed stream, and a filtrate comprising p-xylene at a concentration lower than the C8 aromatic hydrocarbon feed stream and ethylbenzene at a concentration higher than the C8 aromatic feed stream, the p-xylene product stream is considered rich in p-xylene and depleted in ethylbenzene, and the filtrate is considered depleted in p-xylene and rich in ethylbenzene, compared to the C8 aromatic hydrocarbon feed stream.

The "beginning phase" of a transalkylation process, as used herein, means the initial period of the transalkylation process after a load of fresh or regenerated catalyst starts to be exposed to the transalkylation reaction conditions. In certain embodiments, the beginning phase can range from several hours to several months, e.g., 2 hours to 6 months. In other examples, the beginning phase can range from 8 hours to 180 days, from 10 hours to 120 days, or from 12 hours to 90 days, or from 18 hours to 60 days, or from 24 hours to 30 days, or from 36 hours to 15 days, or from 48 hours to 7 days.

"Consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

In various embodiments of the transalkylation process of this disclosure, a C9+ aromatic feed and a C6-C7 aromatic hydrocarbon feed is supplied into a transalkylation reactor having a transalkylation catalyst disposed therein. In the presence of the transalkylation catalyst and under transalkylation conditions, the C9+ aromatic hydrocarbons exchange methyl group(s) with benzene and/or toluene to produce a transalkylation produce mixture comprising benzene, toluene, xylenes, and C9+ aromatic hydrocarbons. Some of the C9+ aromatic hydrocarbons may comprise C2+ alkyl groups attached to an aromatic ring therein and/or an aliphatic ring annelated to an aromatic ring therein. To convert such aromatic hydrocarbons into useful products, the transalkylation catalyst and transalkylation conditions can be chosen such that at least a portion of the C2+ alkyl groups and/or the aliphatic ring are removed from the aromatic ring via dealkylation in the presence of molecular hydrogen ($H_2$) fed into the transalkylation reactor. Such dealkylation produces light hydrocarbons. In the transalkylation reactor, undesirable side reactions such as hydrogenation of the aromatic hydrocarbons, and/or scission of aliphatic rings, and the like, can result in the formation of compounds co-boiling with benzene and/or toluene, such as those described earlier in this disclosure. Separation of the transalkylation product mixture to remove molecular hydrogen and the light hydrocarbons can leave an aromatic hydrocarbon-rich mixture comprising benzene and co-boilers thereof, toluene and co-boilers thereof, xylenes, ethylbenzene, and C9+ aromatic hydrocarbons. It is highly desirable that the formation of benzene co-boilers and/or toluene co-boilers in the transalkylation is reduced, so that the aromatic hydrocarbon-rich mixture comprises such co-boilers at a low concentration, and a high-purity benzene product can be produced from it without having to go through a solvent extraction step to remove the co-boilers. The xylenes produced in the transalkylation reactor can be separated to produce highly valuable products such as p-xylene and/or o-xylene.

It has been surprisingly and unexpectedly discovered that introducing sulfolane into a transalkylation reactor along with the aromatic hydrocarbon feed(s) significantly improves the transalkylation product benzene purity. Typically, introduction of a sulfur compound will only improve the benzene purity until the sulfur compound is removed. However, it has been surprisingly and unexpectedly discovered that after terminating the sulfolane addition, the benzene purity remained higher than prior to introduction of the sulfolane. Accordingly, it has been discovered that sulfolane can be used in the transalkylation process to reduce non-aromatics that co-boil with the benzene in the transalkylation product. In certain embodiments, sulfolane may be fed continuously into the transalkylation reactor to achieve a high purity of a benzene product produced at least in part from the transalkylation product mixture. In other embodiments, it is advantageous to introduce sulfolane into the transalkylation reactor for a given period of time, especially in the beginning phase of a transalkylation catalyst cycle, and then ceasing the introduction afterwards.

In certain embodiments, the sulfolane can be fed into the transalkylation reactor for a period of time (the "first period of time"), e.g., from t1 to t2 day(s), where t1 and t2 can be, e.g., 1, 2, 3, 4, 5, 6, 7, 8, 9, 10, 11, 12, 13, 14, as long as t1<t2. Since sulfolane can inhibit the activity of the transalkylation catalyst resulting in reduction of conversion of C9+ aromatic hydrocarbons, a relatively short period of, e.g., 1 to 10 days, 1 to 8 days, 1 to 6 days, 1 to 5 days, 1 to 3 days, and the like, maybe desirable. For the same reason it is desirable in various embodiments to cease the introduction of sulfolane after the first period of time. To achieve a long residual effect of enhancing benzene product purity, a period of at least one day, or at least 2 days, or even at least 3 days, is highly desired. A particularly advantageous first period of time is from 3 to 6 days.

The quantity of sulfolane fed into the transalkylation reactor can vary broadly in the process of this disclosure, e.g., from c1 to c2 ppm by weight, based on the total weight of the C9+ aromatic feed, the sulfolane, and the at least one of benzene and toluene supplied into the transalkylation reactor, wherein c1 and c2 can be, e.g., 50, 60, 70, 80, 90, 100, 110, 120, 130, 140, 150, 160, 170, 180, 190, 200, 220, 240, 250, 260, 280, 300, 320, 340, 350, 360, 380, or 400, as long as c1<c2. To achieve an appreciable benzene quality enhancement, it is highly desired that the quantity of sulfolane fed into the transalkylation reactor is at least 50 ppm. At relatively low sulfolane feeding quantity, e.g., ≤180 ppm, ≤160 ppm, ≤150 ppm, ≤140 ppm, ≤120 ppm, or ≤100 ppm, the reduction of C9+ aromatic hydrocarbon conversion resulting from co-feeding sulfolane can be reversed upon ceasing introduction of sulfolane into the transalkylation reactor. A particularly advantageous quantity of sulfolane fed into the transalkylation reactor is from 70 to 200 ppm. At higher quantity of sulfolane fed into the transalkylation reactor, the benzene purity enhancement can be more significant. At high sulfolane feeding quantity, e.g., ≥200 ppm, ≥250 ppm, ≥300 ppm, ≥350 ppm, especially if coupled with a lengthy first period of time of exposure, e.g., ≥6 days, ≥8 days, ≥10 days, and the like, permanent loss of catalyst activity can result, resulting in permanent impairment to C9+ aromatic hydrocarbon conversion even upon ceasing sulfolane introduction, which can be undesirable.

It has been found that in the beginning phase of a transalkylation process (i.e., in proximity to a start of a transalkylation catalyst cycle), when the transalkylation catalyst is fresh or newly regenerated, the catalyst can have a high activity, resulting in high conversion of the C9+ aromatic and high selectivity for benzene co-boilers and/or toluene co-boilers. Thus, the transalkylation process of this disclosure can be particularly advantageous where the first period of time of co-feeding sulfolane into the transalkylation reactor is in proximity to the start of a catalyst cycle of the transalkylation catalyst. Thus, the first period of time may begin before, simultaneously, or shortly after the transalkylation catalyst is first exposed to transalkylation conditions in a catalyst cycle.

In certain embodiments, at least a portion (e.g., ≥50%, ≥80%, ≥90%, or the entirety) of the sulfolane fed into the transalkylation reactor along with the aromatic feed(s) can be in a form a sulfolane stream separate from the C9+ aromatic feed and the benzene/toluene feed. Alternatively or additionally, at least a portion (e.g., ≥50%, ≥80%, ≥90%, or the entirety) of the sulfolane feed fed into the transalkylation reactor can be entrained in the benzene/toluene feed(s) as a portion (e.g., a contaminant) thereof. For example, the sulfolane may be entrained in the benzene/toluene feed(s) produced from a solvent extraction process using sulfolane as an extraction solvent. Alternatively or additionally, at least a portion (e.g., ≥50%, ≥80%, ≥90%, or the entirety) of the sulfolane feed fed into the transalkylation reactor can be entrained in the C9+ aromatic feed as a portion (e.g., a contaminant) thereof.

In certain embodiments of the process of this disclosure, at least a portion of the transalkylation product mixture is supplied into a distillation column, preferably without an intermediate solvent extraction step before the at least a portion of the transalkylation product mixture is supplied to the distillation column, and a benzene product stream is produced from the distillation column. Desirably, the benzene product stream has a benzene purity of ≥98.00 wt %, ≥98.20 wt %, ≥98.40 wt %, ≥98.50 wt %, ≥98.60 wt %, ≥98.80 wt %, ≥99.00 wt %, ≥99.10 wt %, ≥99.20 wt %, ≥99.30 wt %, ≥99.40 wt %, ≥99.50 wt %, ≥99.60 wt %, ≥99.70 wt %, ≥99.80 wt %, ≥99.81 wt %, ≥99.82 wt %, ≥99.83 wt %, ≥99.84 wt %, ≥99.85 wt %, ≥99.86 wt %, ≥99.87 wt %, ≥99.88 wt %, ≥99.89 wt %, or even ≥99.90 wt %. The process of this disclosure, by co-feeding a quantity of sulfolane into the transalkylation reactor, enables such high benzene purity of the benzene product produced from the transalkylation product mixture without an intermediate solvent extraction step.

The Feeds Supplied to the Transalkylation Reactor

Desirably the C9+ aromatic feed comprises C9+ aromatic hydrocarbons at ≥60 wt %, ≥70 wt %, ≥75 wt %, ≥80 wt %, ≥85 wt %, ≥90 wt %, or ≥95 wt %, based on the total weight of the C9+ aromatic feed. Desirably the C9+ aromatic feed comprises C9-C11 aromatic hydrocarbons at ≥60 wt %, ≥70 wt %, ≥75 wt %, ≥80 wt %, ≥85 wt %, ≥90 wt %, or ≥95 wt %, based on the total weight of the C9+ aromatic feed. Desirably the C9+ aromatic feed comprises C9-C10 aromatic hydrocarbons at ≥60 wt %, ≥70 wt %, ≥75 wt %, ≥80 wt %, ≥85 wt %, ≥90 wt %, or ≥95 wt %, based on the total weight of the C9+ aromatic feed.

In certain embodiments, the C9+ aromatic feed may comprise C8 aromatic hydrocarbons such as ethylbenzene at various quantity. Desirably the C9+ aromatic feed comprises ≤20 wt %, ≤15 wt %, ≤10 wt %, ≤8 wt %, ≤5 wt %, ≤3 wt %, of C8 aromatic hydrocarbons.

The C9+ aromatic hydrocarbon contained in the C9+ aromatic feed may comprise: C9 aromatic hydrocarbons such as trimethylbenzenes, methylethylbenzenes, n-propylbenzene, cumene, indane, and the like; C10 aromatic hydrocarbons such as tetramethylbenzenes, ethyldimethylbenzenes, diethylbenzenes, n-propylmethylbenzenes, methylcumenes (i-propylmethylbenzenes), naphthalene, tetralin, methylindanes, and the like; and C11 aromatic hydrocarbons such as pentamethylbenzene, methyldiethylbenzenes, ethyltrimethylbenzenes, methylnaphthalenes, dimethylindanes, methyltetralins, and the like. The C9+ aromatic feed can be a C9+ fraction from any refinery process that is rich in aromatics. This aromatics fraction can contain a substantial proportion of C9+ aromatics, e.g., at least 80 wt % C9+ aromatics, where at least 80 wt % or at least 90 wt %, of the hydrocarbons range from C9 to C12. Typical refinery fractions that may be useful can include catalytic reformate, FCC naphtha, and/or TCC naphtha.

In the transalkylation process of this disclosure, at least one of benzene and toluene is fed into the transalkylation reactor. The benzene/toluene feed can desirably react with the C9+ aromatic hydrocarbons to produce more valuable molecules such as xylenes. In certain embodiments, the at least one of benzene and toluene fed into the transalkylation reactor comprises ≥90 wt %, ≥92 wt %, ≥95 wt %, ≥96 wt %, ≥98 wt %, or even ≥99 wt % of benzene, based on the total weight of benzene and toluene fed into the transalkylation reactor.

In other embodiments, the at least one of benzene and toluene fed into the transalkylation comprises ≥80 wt %, ≥84 wt %, ≥85 wt %, ≥88 wt %, ≥90 wt %, ≥92 wt %, ≥94 wt %, ≥95 wt %, ≥98 wt %, or even ≥99 wt % of toluene, based on the total weight of benzene and toluene fed into the transalkylation reactor. In other embodiments, the at least one of benzene and toluene can be a mixture of benzene and toluene at any other weight percentages. The at least one of benzene and toluene can be fed into the transalkylation reactor as a C6-C7 aromatic hydrocarbon stream, a toluene-rich stream, and the like. A toluene-rich stream can be advantageously used as the source of the at least one of benzene and toluene in the process of this disclosure for the purpose of producing a benzene product stream from the transalkylation product mixture.

Depending on the composition of the C9+ aromatic feed and the ratio of benzene/toluene, the weight ratio of the C9+ aromatic feed to the at least one of benzene and toluene can vary widely. In embodiments where the primary purpose is to produce more xylenes from the C9+ aromatic hydrocarbons, it may be highly desirable that benzene and/or toluene may be used at an excess quantity relative to the C9+ aromatic hydrocarbon to obtain a high conversion of the C9+ aromatic hydrocarbons and a high yield of xylenes. In embodiments where the production of a benzene product is a major objective, the at least one of benzene and toluene can be a toluene-rich stream, and toluene may be used at an excessive quantity relative to the C9+ aromatic hydrocarbons such that the C9+ aromatic hydrocarbons are converted into xylenes and benzene at a high conversion.

In certain embodiments, the transalkylation feed can contain ethylbenzene, C9+ aromatics hydrocarbons and toluene. The transalkylation feed can also include recycled/unreacted/produced benzene, toluene, ethylbenzene, and/or C9+ aromatics that is obtained by distillation of the effluent product of the transalkylation reaction itself. Toluene can constitute from 5 wt % to 90 wt % of the transalkylation feed and C9+ can constitute from 10 wt % to 95 wt % of the transalkylation fee. In a light feed, toluene can constitute from 40 wt % to 90 wt %, such as from 50 wt % to 70 wt % of the transalkylation feed, whereas the C9+ aromatics component can constitute from 10 wt % to 60 wt %, such as from 30 wt % to 50 wt %, of the transalkylation feed. In a heavy feed, toluene can constitute from 15 wt % to 50 wt %, such as from 25 wt % to 40 wt % of the transalkylation feed, whereas the C9+ aromatics component constitutes from 50 wt % to 85 wt %, such as from 60 wt % to 75 wt %, of the transalkylation feed.

The Transalkylation Process

The transalkylation process can be conducted in any appropriate reactor including a radial flow, fixed bed, continuous flow, or fluid bed reactor. The transalkylation reaction conditions can include a reactor inlet temperature of 200° C. to 550° C., such as 343° C. to 510° C. or 400° C. to 454° C. The transalkylation reaction conditions can include an absolute pressure from 380 kPa to 4,240 kPa, such as from 1,480 kPa to 3,550 kPa. The transalkylation reaction conditions can include a hydrogen to hydrocarbon molar ratio of 1 to 10, 1.5 to 10, 1 to 5, or 1 to 3. The transalkylation reaction conditions can include a weight hour space velocity (WHSV) of 0.2 $h^{-1}$ to 20 $h^{-1}$, such as from 1 $h^{-1}$ to 5 $h^{-1}$. The transalkylation reaction conditions can be sufficient to convert the aromatic feed to a product containing C6-C8 aromatic compounds, such as benzene, toluene and xylenes, especially benzene and xylene. The transalkylation reaction conditions also can be sufficient to convert the ethylbenzene in the transalkylation feed to benzene and ethane.

A desirable category of reactions in the transalkylation process is the exchange of methyl group(s) between and among the C9+ aromatic hydrocarbons and benzene/toluene to produce valuable xylene molecules exemplified below:

Trimethylbenzenes+Benzene→Xylenes+Toluene
Trimethylbenzenes+Toluene→Xylenes
Tetramethylbenzenes+Toluene→Xylenes+Trimethylbenzenes
Ethylmethylbenzenes+Toluene→Xylenes+Ethylbenzene
Ethyldimethylbenzenes+Toluene→Xylenes+Ethylmethylbenzenes
Toluene+Toluene→Xylenes+benzene Another category of reactions in the transalkylation process is the dealkylation of C2+ alkyl group(s) contained in some of the C9+ aromatic hydrocarbons exemplified below, which can produce significant quantity of benzene:

n-propylbenzene+$H_2$→Benzene+Propane
Cumene+$H_2$→Benzene+Propane
Ethylbenzene+$H_2$→Benzene+Ethane
Ethylmethylbenzenes+$H_2$→Toluene+Ethane
Diethylbenzenes+$H_2$→Benzene+Ethane
Ethyldimethylbenzenes+$H_2$→Xylenes+Ethane Transalkylation Catalyst The transalkylation catalyst can contain at least one transalkylation component and at least one hydrogenation component, and optionally at least one inorganic binder. The transalkylation component can be a solid acid such as a molecular sieve, e.g., an aluminosilicate molecular sieve selected from the following framework types: CHA, EMT, ERI, EUO, FAU, FER, HEU, KFI, LEV, LTA, MAZ, MEI, MEL, MF, MTT, MTW, MWW, TON, and mixtures and combinations thereof.

The hydrogenation component can be, e.g., a metal selected from nickel, rhodium, palladium, ruthenium, rhenium, osmium, iridium, platinum, and mixtures and combinations thereof.

The inorganic binder can be selected from oxides of metals of Groups 1, 2, 3, 5, 6, 14, and 15, and mixtures, combinations and compounds thereof. Non-limiting examples of the inorganic binder can be: alumina, silica, zirconia, titania, mixtures and combinations thereof, and their compounds with one or more of oxides of alkali metals, oxides of alkaline earth metals, $P_2O_5$, and the like.

In certain embodiments, the transalkylation catalyst can be a catalyst system that includes two or more catalysts. For example, the catalyst system can include: (a) a first catalyst that can include a first molecular sieve having 0.01 wt % to 5 wt % of at least one source of a first metal element of Groups 6-10 and a Constraint Index of 3-12; and (b) a second catalyst that can include a second molecular sieve having 0 to 5 wt % of at least one source of a second metal element of Groups 6-10 and a Constraint Index less than 3 and, where the weight ratio of the first catalyst over the second catalyst is in the range of 5:95 to 75:25, and where the C9+A feedstock and the C6A/C7A feedstock in the present of hydrogen can contact the first catalyst prior to contacting the second catalyst.

The Constraint Index is a measure of the extent to which an aluminosilicate or molecular sieve provides controlled access to molecules of varying sizes to its internal structure. For example, aluminosilicates that provide a highly restricted access to and egress from its internal structure have a high value for the constraint index, and aluminosilicates of this kind usually have pores of small size, e.g., less than 5 Angstroms. On the other hand, aluminosilicates that provide relatively free access to the internal aluminosilicate structure have a low value for the constraint index, and usually pores of large size. The method by which constraint index is determined is described in U.S. Pat. No. 4,016,218.

A molecular sieve having a Constraint Index of 3-12 (as defined in U.S. Pat. No. 4,016,218), includes ZSM-5, ZSM-11, ZSM-22, ZSM-23, ZSM-35, ZSM-48, ZSM-57, and ZSM-58. ZSM-5 is described in U.S. Pat. No. 3,702,886 and Re. 29,948. ZSM-11 is described in U.S. Pat. No. 3,709,979. ZSM-22 is described in U.S. Pat. Nos. 4,556,477 and 5,336,478. ZSM-23 is described in U.S. Pat. No. 4,076,842. ZSM-35 is described in U.S. Pat. No. 4,016,245. ZSM-48 is described in U.S. Pat. Nos. 4,234,231 and 4,375,573. ZSM-57 is described in U.S. Pat. No. 4,873,067. ZSM-58 is described in U.S. Pat. No. 4,698,217.

A molecular sieve having a Constraint Index of less than 3 (as defined in U.S. Pat. No. 4,016,218), includes zeolite beta, zeolite Y, Ultrastable Y (USY), Dealuminized Y (Deal Y), mordenite, ZSM-3, ZSM-4, ZSM-12, ZSM-18, NU-87, and ZSM-20. Zeolite ZSM-4 is described in U.S. Pat. No. 3,923,636. Zeolite ZSM-12 is described in U.S. Pat. No. 3,832,449. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is described in U.S. Pat. Nos. 3,766,093 and 3,894,104.

In certain embodiments, the first molecular sieve can be a ten member ring molecular sieve and the second molecular sieve can be a twelve member ring molecular sieve. Examples of ten member ring molecular sieve are ZSM-5, ZSM-11, ZSM-22, ZSM-23, ZSM-35, ZSM-48, ZSM-57, and ZSM-58. Examples of twelve member ring molecular sieve are zeolite beta, zeolite Y, Ultrastable Y (USY), Dealuminized Y (Deal Y), mordenite, ZSM-3, ZSM-4, ZSM-12, ZSM-18, NU-87, and ZSM-20.

With regard to the molecular sieve having a Constraint Index of less than 3, ZSM-12 is described in U.S. Pat. No. 3,832,449. Mordenite occurs naturally but may also be used in one of its synthetic forms, such as TEA-mordenite (i.e., synthetic mordenite prepared from a reaction mixture comprising a tetraethylammonium directing agent), which is described in U.S. Pat. Nos. 3,766,093 and 3,894,104. Examples of suitable porous crystalline inorganic oxide materials having the defined X-ray diffraction pattern include MCM-22, PSH-3, SSZ-25, MCM-36, MCM-49 or MCM-56. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575, and MCM-56 is described in U.S. Pat. No. 5,362,697.

In certain embodiments, the first catalyst can include at least 1 wt %, at least 10 wt %, at least 50 wt %, or at least 65 wt %, of the first molecular sieve. The second catalyst can include at least 1 wt %, at least 10 wt %, at least 50 wt %, or at least 65 wt %, of the second molecular sieve.

The catalyst system can have a weight ratio of the first catalyst over the second catalyst of 5:95 to 75:25, 10:90 to 60:40, or 20:80 to 50:50.

In certain embodiments, the first molecular sieve can have an Alpha value of at least 150, such as at least 300. In other examples, the first molecular sieve can have an Alpha value in the range of 100-1500, preferably in the range of 300-600.

Where the first molecular sieve is ZSM-5, the ZSM-5 can have a composition involving the molar ratio of $YO_2$ over $X_2O_3$ of n, wherein X is a trivalent element, such as aluminum, boron, iron, indium and/or gallium, preferably aluminum; Y is a tetravalent element, such as silicon, tin and/or germanium, preferably silicon; and n is less than 1000, such as from 10 to less than 100. The ZSM-5 may further be selected so as to have an average crystal size of less than 0.1 micron, such as 0.05 micron, and a Diffusion Parameter, D/r2, for mesitylene of at least $1000 \times 10^{-6}$ sec$^{-1}$, such as at least $2000 \times 10^{-6}$ sec$^{-1}$, when measured at a temperature of 100° C. and a mesitylene pressure of 2 torr.

In certain embodiments, the first molecular sieve can be ZSM-5 and the second molecular sieve can be ZSM-12. Where the second molecular sieve is ZSM-12, the ZSM-12 can have a composition involving the molar YO2 over X2O3=n, wherein X is a trivalent element, such as aluminum, boron, iron, indium and/or gallium, preferably aluminum; Y is a tetravalent element, such as silicon, tin and/or germanium, preferably silicon; and n is less than 500, such as from 50 to less than 300. The ZSM-12 may further be selected so as to have an average crystal size of less than 0.1 micron, such as 0.05 micron, and a Diffusion Parameter, D/r2, for mesitylene of at least $1000 \times 10^{-6}$ sec$^{-1}$, such as at least $2000 \times 10^{-6}$ sec$^{-1}$, when measured at a temperature of 100° C. and a mesitylene pressure of 2 torr.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus, for a given sorbate loading Q, the value Q/Q', where Q' is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

In certain embodiments, the second molecular sieve can have an Alpha value of at least 20, such as at least 30. In other embodiments, the second molecular sieve has an Alpha value in from 20 to 500, from 20 to 100, or from 40 to 100 or from 30 to 100.

The Alpha value a measure of the cracking activity of a catalyst and a method of determining the Alpha value is described in U.S. Pat. No. 3,354,078 and in the Journal of Catalysis, Vol. 4, p. 527 (1965); Vol. 6, p. 278 (1966); and Vol. 61, p. 395 (1980).

It may be desirable to incorporate each molecular sieve in the catalyst composition with another material that is resistant to the temperatures and other conditions employed in the transalkylation process of the disclosure. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

Use of a material in conjunction with each molecular sieve, i.e., combined therewith or present during its synthesis, which itself is catalytically active, may change the conversion and/or selectivity of the catalyst composition. Inactive materials can serve as diluents to control the amount of conversion so that transalkylation products can be obtained in an economical and orderly manner without employing other means for controlling the rate of reaction. These catalytically active or inactive materials can be incorporated into, for example, naturally occurring clays, e.g., bentonite and kaolin, to improve the crush strength of the catalyst composition under commercial operating conditions. It can be desirable to provide a catalyst composition having good crush strength because in commercial use, it can be desirable to prevent the catalyst composition from breaking down into powder-like materials.

Naturally occurring clays that can be composited with each molecular sieve as a binder for the catalyst composition include the montmorillonite and kaolin family, which families include the subbentonites, and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment, and/or other chemical modification.

In addition to the foregoing materials, each molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

In certain embodiments, each molecular sieve can be admixed with the binder or matrix material so that the final catalyst composition contains the binder or matrix material in an amount of 5 wt % to 95 wt %, e.g., 10 wt % to 60 wt % based on the total weight of the catalyst and binder or matrix material.

In certain embodiments, the first catalyst can contain 0.01 to 5 wt %, 0.1 to 2 wt % or 0.1 to 1 wt % based on the weight of the first catalyst, of a first metal element of Groups 6-10. The second catalyst can contain 0 to 5 wt %, 0.01 to 2 wt %, or 0.01 to 1 wt % based on the weight of the second catalyst, of a second metal element of Groups 6-10. The first metal element and the second metal element can be at least one hydrogenation component, such as tungsten, vanadium, molybdenum, rhenium, chromium, manganese, a metal selected from Groups 6-10 of the Periodic Table of the Elements, or mixtures thereof. Specific examples can include iron, ruthenium, rhenium, osmium, nickel, cobalt, rhodium, iridium, and noble metals such as platinum or palladium. The hydrogenation component can be palladium, platinum, rhenium or combinations thereof.

In certain embodiments, the amount of the hydrogenation component can be selected according to a balance between hydrogenation activity and catalytic functionality. Less of the hydrogenation component is required when the most active metals such as platinum are used as compared to palladium, which does not possess such strong hydrogenation activity. The catalyst composition can contain less than 5 wt % of the hydrogenation component and in certain embodiments from 0.01 wt % to 2 wt % of the component.

In certain embodiments, the hydrogenation component can be incorporated into the catalyst composition by co-crystallization, exchanged into the composition to the extent a Group 13 element, e.g., aluminum, is in the molecular sieve structure, impregnated therein, or mixed with the molecular sieve and binder. Such component can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum amine complex, such as $Pt(NH_3)_4Cl_2.H_2O$.

In certain embodiments, a compound of the hydrogenation component may be added to the molecular sieve when it is being composited with a binder, or after the molecular sieve and binder have been formed into particles by extrusion or pelletizing.

In certain embodiments, after treatment with the hydrogenation component, the molecular sieve can be dried by heating at a temperature of 65° C. to 160° C., 110° C. to 143° C., for at least 1 minute and generally not longer than 24 hours, at an absolute internal pressure in a range from 100 kPa to 200 kPa. Thereafter, the molecular sieve can be calcined in a stream of dry gas, such as air or nitrogen, at temperatures of from 260° C. to 650° C. for 1 to 20 hours. Calcination can be conducted at an absolute internal pressures ranging from 100 kPa to 300 kPa.

In certain embodiments, prior to use, steam treatment of the catalyst composition can be employed to minimize the aromatic hydrogenation activity of the catalyst composition. In the steaming process, the catalyst composition can be contacted with steam, at a temperature of at least 260° C. to 650° C. for at least one hour, specifically at least 1 to 20 hours, at an absolute pressure of 100 kPa to 2,590 kPa.

FIG. 1 schematically illustrates a process 101 for making xylenes, particularly a p-xylene product stream, and a benzene product stream, from a reformate stream, including a transalkylation step. In this figure, a heavy naphtha stream 103 produced from a crude oil refining process is supplied into a reforming zone 105. The heavy naphtha stream 103 may comprise as a majority paraffins and naphthenes, and as a minority aromatic hydrocarbons. The reforming zone 105 can include one or more of any conventional naphtha catalytic reforming reactor(s), e.g., fixed-bed reactor(s), known in the art. A reforming catalyst is disposed in the reforming zone. On contacting the reforming catalyst under the reforming conditions such as those generally known in the art, hydrocarbons in the heavy naphtha stream 103 undergo a series of chemical reactions, including but not limited to isomerization, aromatization, dehydrocyclization, and the like, whereby at least a portion of the paraffins and naphthenes are converted into aromatic hydrocarbons. A reforming effluent 107 comprising C6+ aromatic hydrocarbons (including benzene, toluene, xylenes, ethylbenzene, and C9+ aromatic hydrocarbons) including such non-methylated substituted aromatic hydrocarbons can be obtained from the reforming zone. In addition to aromatic hydrocarbons, the reforming effluent 107 may comprise non-aromatic hydrocarbons such as alkanes and naphthenes. Preferably the reforming effluent 107 consists essentially of C6+ hydrocarbons. The reforming effluent 107 is interchangeably called a reformate stream herein. Additional streams, such as a hydrogen stream (not shown), and an off-gas stream comprising light hydrocarbons (e.g., C5-hydrocarbons) (not shown), may be produced from the reforming zone as well. Heavy naphtha reforming processes, catalysts, and conditions are disclosed in, e.g., U.S. Pat. Nos. 3,729,408; 3,806,443; 4,354,925; 4,440,628; 4,634,515; 4,927,525; 5,292,976; 5,980,731, the contents of all of which are incorporated herein by reference.

As shown in FIG. 1, the reforming effluent 107 or a portion thereof is then supplied into a reformate splitter 109 (e.g., a single distillation column, or a series of distillation columns), from which a C6-C7 hydrocarbons-rich stream 111 and a C8+ aromatic hydrocarbons-rich stream 113 are produced. The C6-C7 hydrocarbons-rich stream 111 comprises benzene, toluene, and their co-boiling paraffins and naphthenes, and the like. The C8+ aromatic hydrocarbons-rich stream 113 can comprise C8 aromatic hydrocarbons (e.g., xylenes and ethylbenzene), C9 aromatic hydrocarbons (e.g., trimethylbenzenes, ethylmethylbenzenes, n-propylbenzene, cumene, and indane), C10 aromatic hydrocarbons (e.g., tetramethylbenzenes, diethylbenzenes, ethyldimethylbenzenes, methyl-(n-propyl)benzenes, methylcumenes, n-butylbenzene, isobutyl benzene, sec-butylbenzene, tert-butylbenzene, methylindanes, tetralin, and naphthalene), and even C11+ aromatic hydrocarbons (e.g., methylnaphthalenes, methyltetralins). The C8+ aromatic hydrocarbons-rich stream 113, optionally in combination with other C8+ aromatics-rich stream(s) such as stream 145 (described below) as a joint stream 114, is then supplied to a xylenes splitter 115 (e.g., one or more distillation columns), from which a xylenes-rich stream 117 and a C9+ aromatic hydrocarbons-rich stream 129 are produced.

The joint stream 114 is rich in C8+ aromatic hydrocarbons and lean in benzene, toluene, and co-boilers thereof compared to stream 107. The xylenes-rich stream 117 comprises xylenes and ethylbenzene. Stream 117 can comprise p-xylene and ethylbenzene at various concentrations, depending on the composition(s) of the C8+ aromatic hydrocarbons-rich stream(s) supplied to the xylenes splitter 115.

As shown in FIG. 1, for the purpose of production of a p-xylene product, the xylenes-rich stream 117 is typically supplied to a p-xylene recovery sub-system 119, from which a p-xylene product stream 121 rich in p-xylene and a p-xylene depleted stream 123 are produced. The p-xylene recovery sub-system 119 can be any crystallization-based or adsorption chromatography-based p-xylene separation systems known in the art. The first p-xylene depleted stream 123, rich in m-xylene, o-xylene, and ethylbenzene compared to stream 117, is typically at least partly supplied to an isomerization zone 125 containing an isomerization catalyst disposed therein. On contacting the isomerization catalyst under isomerization conditions, a portion of the m-xylene and o-xylene in stream 125 supplied into the isomerization zone 125 are converted into p-xylene. The isomerization effluent 127 exiting the isomerization zone 125 comprises p-xylene at a concentration higher than the p-xylene depleted stream 123. The isomerization effluent 127, or a portion thereof, is then supplied to the xylenes splitter 115. The xylenes splitter 115, the p-xylene recovery sub-system 119, and the isomerization zone 125 form a xylenes-loop.

As shown in FIG. 1, the C9+ aromatic hydrocarbons-rich stream 129 produced from the xylenes splitter 115, typically containing C9, C10, and C11+ aromatic hydrocarbons, can be then separated in an optional distillation column 131 to obtain a C9-C10 aromatic hydrocarbons-rich stream 133 and a C11+ aromatic hydrocarbons-rich stream 135. Stream 135 is typically conducted away and used as, e.g., a motor gasoline blending stock, a fuel oil, and the like. Stream 133, along with a benzene/toluene-rich stream 146, is then supplied into a transalkylation zone 147 having a transalkylation catalyst disposed therein. Alternatively, at least a portion of stream 129, without further separation in column 131, may be supplied directly into the transalkylation zone 147.

In the presence of the transalkylation catalyst and under transalkylation conditions, the C9+ aromatic hydrocarbons react with benzene/toluene to produce xylenes. The C9+ aromatic hydrocarbons typically comprises aromatic hydrocarbons having an C2+ alkyl group attached to an aromatic ring therein (e.g., ethylmethylbenzene, ethyldimethylbenzene, diethylbenzene, n-propylbenzene, cumene, and the like) or an aliphatic ring annelated to an aromatic ring therein (indane, methylindanes, tetralin, and the like). In order to convert these aromatic hydrocarbons into useful products, the transalkylation catalyst and transalkylation conditions are typically chosen to dealkylate the C2+ alkyl groups and/or the aliphatic rings from the aromatic rings to in the presence of molecular hydrogen. Such dealkylation produces light hydrocarbons. Thus the transalkylation effluent exiting the transalkylation zone typically comprises light hydrocarbons and hydrogen. A stream 148 rich in light hydrocarbons and hydrogen can be produced. Stream 149, rich in xylenes and comprising benzene and toluene, can be supplied to a benzene splitter 141, from which a benzene product stream 143, a toluene-rich stream 146, and a C8+ aromatic hydrocarbons-rich stream 145, are produced. The toluene-rich stream 146, or a portion thereof, can be supplied to the transalkylation zone 147, for the purpose of producing additional quantity of xylenes and/or benzene.

It is highly desirable that the benzene product stream 143 has a high benzene purity of, e.g., ≥98.00 wt %, ≥98.30 wt %, ≥98.50 wt %, ≥98.80 wt %, ≥99.00 wt %, ≥99.10 wt %, ≥99.20 wt %, ≥99.30 wt %, ≥99.40 wt %, ≥99.50 wt %, ≥99.60 wt %, ≥99.70 wt %, ≥99.80 wt %, ≥99.82 wt %, ≥99.84 wt %, ≥99.85 wt %, ≥99.86 wt %, ≥99.88 wt %, ≥99.90 wt %, ≥99.92 wt %, ≥99.94 wt %, or even ≥99.95 wt %, based on the total weight of the benzene stream 143. Benzene purity is calculated as the weight percentage of benzene based on the total weight of the benzene stream. To achieve a high benzene purity of stream 143, it is highly desirable that the benzene-containing streams 139 from the benzene-toluene extraction zone 137 and stream 149 derived from the transalkylation zone 147 contain benzene co-boilers at a low concentration. By solvent extraction in zone 137, stream 139 can be made to contain benzene co-boiler at a very low concentration. Thus, one embodiment to improve the benzene product purity in stream 143 is to separate stream 149 to obtain a benzene-toluene-containing stream (now shown), and then feed that stream to the solvent extraction zone 137 to remove benzene and toluene co-boilers therein (now shown).

In the process of this disclosure, however, by co-feeding a quantity of sulfolane into the transalkylation reactor 147 along with the aromatic hydrocarbon feed(s), the concentration of benzene co-boilers in stream 149 is reduced, and benzene purity of stream 143 is enhanced while stream 149 is fed directly to the benzene column 141. As shown in FIG. 1, a sulfolane stream 144 separate from the aromatic hydrocarbon streams 133 and 146 is supplied into transalkylation reactor 147. Alternatively or additionally, the sulfolane can be supplied at least partly (preferably entirely) via the toluene-rich stream 146 produced from the benzene column 141. The sulfolane contained in stream 146 can be at least partly (preferably entirely) sourced from stream 139 rich in benzene and toluene. The sulfolane contained in stream 139, in turn, can be sourced from the sulfolane used as an extraction solvent in the solvent extraction zone 137. Thus, the sulfolane contained in stream 146 can be used to benefit transalkylation in the process of this disclosure without being separated as a contaminant. The presence of sulfolane in the transalkylation reactor inhibits the production of benzene co-boilers in the transalkylation reactor. The presence of sulfolane in the transalkylation reactor can eliminate the need of separating stream 149 to produce a benzene-toluene containing stream, and then supplying the benzene-toluene stream to the solvent extraction zone 137 for the purpose of removing benzene and toluene co-boilers, resulting in significant reduction of equipment need and process complexity and substantial gain in energy efficiency.

As shown in FIG. 1, the C6-C7 hydrocarbons-rich stream 111 separated from the reformate splitter 109 is typically supplied to an extraction distillation zone 137, where a C6-C7 aromatic hydrocarbons-rich stream 139 and an aromatic hydrocarbons-depleted raffinate stream 138 are produced. Stream 139 is then supplied to the benzene tower 141, from which a benzene product stream 143, a toluene-rich stream 146, and a C8+ aromatic hydrocarbons-rich stream 145 are produced. The toluene-rich stream 146, or a portion thereof, is supplied to the transalkylation 147 together with the C9-C10 aromatic hydrocarbons-rich stream 133 as described above. The C8+ aromatic hydrocarbons-rich stream 145 is then supplied to the xylenes splitter 115 along with stream 113, as described above.

This disclosure is further illustrated by the following non-limiting examples.

Example

A liquid feed stream comprising toluene and C9-C10 aromatic hydrocarbons with a toluene/C9-C10 aromatic hydrocarbons weight ratio of 20/80 was heated, vaporized, and fed into a transalkylation reactor along with molecular hydrogen. In the transalkylation reactor a fixed bed catalyst system of a transalkylation catalyst as described in U.S. patent Ser. No. 10/118,165 was installed. Transalkylation in the reactor was carried out in a process as described in U.S. Pat. No. 10,118,165 for an initial period of time of at least 3 days. The relevant portion of U.S. patent Ser. No. 10,118, 165 is incorporated by reference in its entirety. A transalkylation product mixture exited the transalkylation reactor. The product mixture was subsequently cooled, condensed, and separated to obtain a liquid product stream comprising C6+ aromatic hydrocarbons and a vapor stream comprising molecular hydrogen and light hydrocarbons. Composition of the liquid product stream was analyzed using gas chromatography. Conversion of the C9-C10 aromatic hydrocarbons was calculated based on the composition of the liquid product stream and the composition of the liquid feed stream. Purity of the benzene product ("Benzene Purity") in this Example is calculated pursuant to the following formula, based on the concentrations of the various hydrocarbon components in the liquid product stream obtained from gas chromatography:

$$\text{Benzene Purity} = \frac{Cbz}{Cbz + 0.1*Cn6 + 0.7*Cmcp + Cch + 0.6*(Cecp + Cdmcp) + 0.05*Cmch} \times 100\%$$

where:
Cbz is the concentration of benzene;
Cn6 is the concentration of n-hexane;
Cmcp is the concentration of methylcyclopentane;
Cch is the concentration of cyclohexane;
Cecp is the concentration of ethylcyclopentane;
Cdmcp is the concentration of dimethylcyclopentane; and
Cmch is the concentration of methylcyclohexane, all in weight percentages based on the total weight of the liquid product stream. The thus calculated Benzene Purity is believed to be a good indicator of the purity of a benzene product obtainable by separating the liquid product stream using a distillation tower.

Figure 2:
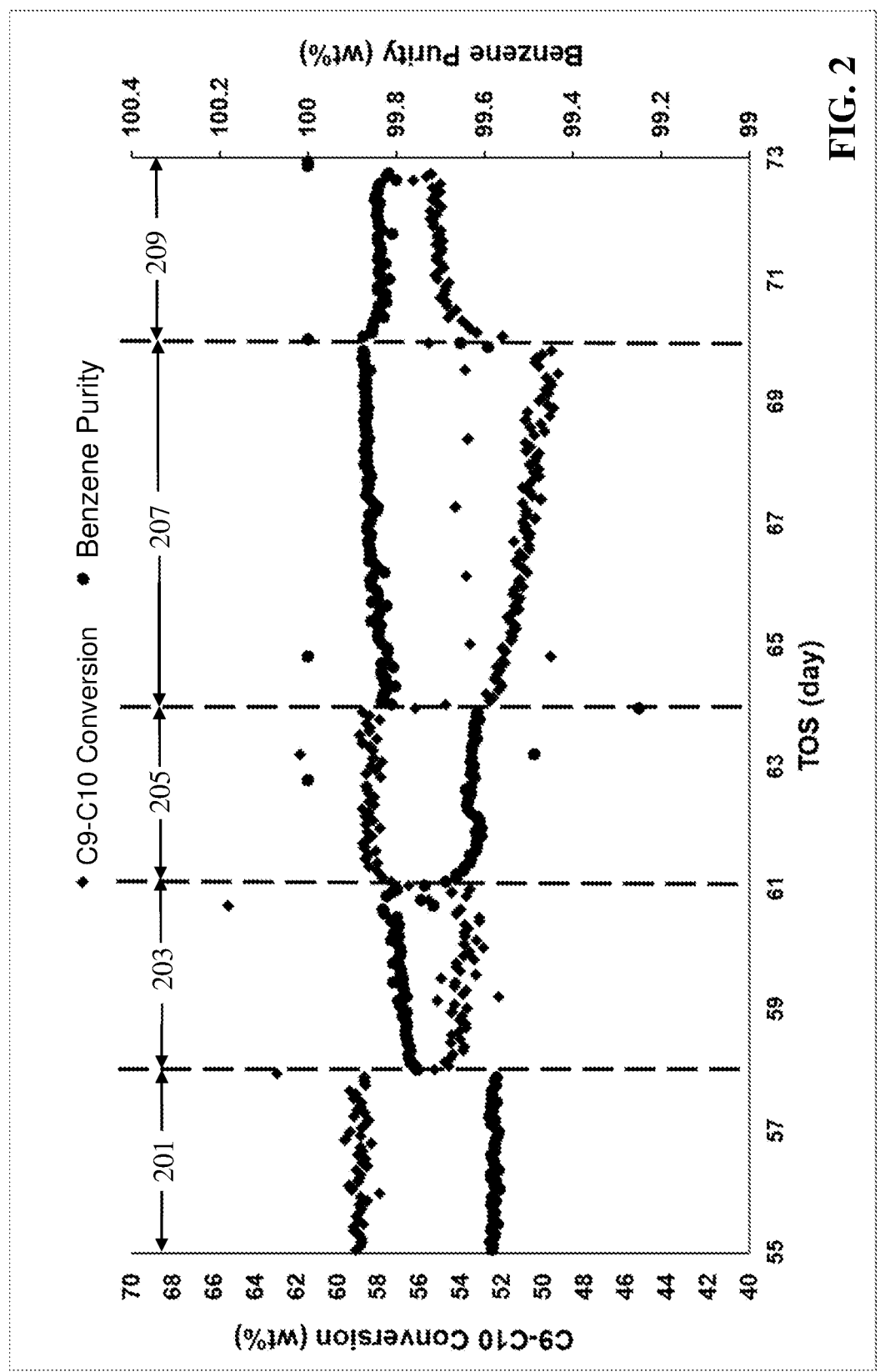
FIG. 2 is graph showing C9-C10 aromatic hydrocarbon conversion and benzene product purity with or without the addition of sulfolane to the transalkylation feed, in a process described in the Example of this disclosure.

The C9-C10 aromatic hydrocarbon conversion (wt %) and benzene purity (wt %) of the process of this Example are shown in FIG. 2.

At the end of the initial period of time (i.e., segment 201), a stream of sulfolane was added into the liquid feed stream at a concentration of 70 ppm, based on the total weight or the liquid feed stream. With the sulfolane stream maintained steady, the transalkylation reactor was allowed to run under the same inlet temperature, WHSV, hydrogen to hydrocarbon molar ratio, and hydrogen partial pressure as in the initial period of time for a first period of time (i.e., segment 203 in FIG. 2) of 3 days, during which conversion of C9-C10 aromatic hydrocarbon and benzene purity of the benzene product stream were monitored and recorded.

At the end of the first period of time, the sulfolane stream fed to the liquid feed stream was stopped. Transalkylation in the reactor was then allowed to run afterwards under the same conditions as in the initial period of time in the absence of a sulfolane stream for a second period of time (i.e., segment 205 in FIG. 2) of 3 days, during which conversion of C9-C10 aromatic hydrocarbon and benzene purity of the benzene product stream were monitored and recorded.

At the end of the second period of time, a sulfolane stream was added into the liquid feed stream at a concentration of 200 ppm, based on the total weight of the liquid feed stream. With the sulfolane stream maintained steady, the transalkylation reactor was allowed to run under the same inlet temperature, WHSV, hydrogen to hydrocarbon molar ratio, and hydrogen partial pressure as in the initial period of time for a third period of time (i.e., segment 207 in FIG. 2) of 6 days, during which conversion of C9-C10 aromatic hydrocarbon and benzene purity of the benzene product stream were monitored and recorded.

At the end of the third period of time, the sulfolane stream added to the liquid feed stream was stopped. Transalkylation in the reactor was allowed to run afterwards under the same conditions as in the initial period of time in the absence of co-fed sulfolane for a fourth period of time (i.e., segment 209 in FIG. 2) of 3 days, during which conversion of C9-C10 aromatic hydrocarbon and benzene purity of the benzene product stream were monitored and recorded.

During the first test in the first period of time (segment 203), C9-C10 aromatic hydrocarbon conversion dropped and transalkylation benzene product purity increased after the introduction of the sulfolane compared to the initial period (segment 201). As shown in FIG. 2, in the presence of co-fed sulfolane at 70 ppm, C9-C10 aromatic hydrocarbon conversion continued to slowly drop while benzene purity slowly increased over the 3 days of the first period of time (segment 203). After the sulfolane introduction was stopped at the end of the first period of time (segment 203), during the second period of time (segment 205), in the absence of sulfolane added into the feed stream, C9-C10 aromatic hydrocarbon conversion recovered close to the value during the initial period of time (segment 201) before the introduction of the sulfolane while benzene purity dropped close to the value during the initial period of time before the sulfolane introduction. A slight improvement (0.02 wt %) was seen in benzene purity during the second period of time (segment 205) compared to the initial period of time (segment 201).

Similarly, during the second test in the third period of time (segment 207), C9-C10 aromatic hydrocarbon conversion dropped and transalkylation benzene product purity increased after the introduction of the sulfolane compared to during the second period of time (segment 205). In the presence of co-fed sulfolane at 200 ppm, C9-C10 aromatic hydrocarbon conversion continued to drop while benzene purity continued to increase while the sulfolane remained in the feed during the third period of time (segment 207). Once the sulfolane introduction was stopped, in the absence of co-fed sulfolane, C9-C10 aromatic hydrocarbon conversion increased while benzene purity decreased in the fourth period of time (segment 209). Due to the longer exposure to sulfolane at a higher dosage in the third period of time (segment 207) compared to in the first period of time (segment 203), permanent conversion decline of approximately 2.5% was seen while benzene purity increased by approximately 0.3% in the fourth period of time (segment 207).

Higher benzene purity was seen when conversion was lower in this Example. The addition of sulfolane into the transalkylation feed at different doses provided an improvement to the overall transalkylation product benzene purity, during sulfolane addition and after ceasing sulfolane addition. This was determined by comparing the benzene purity at the end of the first period of time (segment 203, i.e., the 70 ppm sulfolane addition test), where conversion was 53.8 wt %, to benzene purity at the end of the third period of time (segment 207, i.e., the 200 ppm sulfolane test), where conversion was 55 wt %. A 0.04 wt % benzene purity improvement was seen at the end of the third period of time (segment 207, see Table 1 below), indicating that sulfolane can be used to boost transalkylation product benzene purity.

TABLE 1

| Time | C9-C10 Conversion (wt %) | Benzene Purity (wt %) |
|---|---|---|
| At the end of the initial period (Segment 201) | 59 | 99.58 |
| At the end of the first period (Segment 203) | 54 | 99.80 |
| At the end of the second period (Segment 205) | 58 | 99.61 |

TABLE 1-continued

| Time | C9-C10 Conversion (wt %) | Benzene Purity (wt %) |
|---|---|---|
| At the end of the third period (Segment 207) | 50 | 99.87 |
| At the end of the fourth period (Segment 209) | 55 | 99.84 |

This disclosure may include one or more of the following non-limiting embodiments:

A1. A transalkylation process comprising:
introducing a C9+ aromatic feed, sulfolane, molecular hydrogen ($H_2$), and at least one of benzene and toluene into a transalkylation reactor having a transalkylation catalyst disposed therein; and
contacting the C9+ aromatic feed, the sulfolane, and the at least one of benzene and toluene with the transalkylation catalyst for a first period of time under transalkylation conditions to produce a product mixture.

A2. The process of A1, wherein the first period of time is from 1 day to 14 days.

A3. The process of A1 or A2, wherein the first period of time is from 3 days to 6 days.

A4. The process of any of the preceding embodiments, wherein the first period of time begins in proximity to a start of a catalyst cycle of the transalkylation catalyst.

A5. The process of any of the preceding embodiments, further comprising ceasing introducing sulfolane into the transalkylation reactor at the end of the first period of time.

A6. The process of any of the preceding embodiments, wherein the sulfolane is introduced into the transalkylation reactor at a quantity of from 50 ppm to 400 ppm, based on the total weight of the C9+ aromatic feed, the sulfolane, and the at least one of benzene and toluene.

A7. The process of any of the preceding embodiments, wherein the sulfolane is fed into the transalkylation reactor at a quantity of from 70 ppm to 200 ppm, based on the total weight of the C9+ aromatic feed, the sulfolane, and the at least one of benzene and toluene.

A8. The process of any of the preceding embodiments, wherein the C9+ aromatic feed consists essentially of C9+ aromatic hydrocarbons.

A9. The process of any of the preceding embodiments, wherein the at least one of benzene and toluene is toluene.

A10. The process of any of the preceding embodiments, wherein the at least of one of benzene and toluene is benzene.

A11. The process of any of the preceding embodiments, wherein the at least of one of benzene and toluene is a mixture of benzene and toluene.

A12. The process of any of the preceding embodiments, further comprising:
supplying at least a portion of the product mixture into a distillation column; and
obtaining a benzene product stream from the distillation column.

A13. The process of A12, wherein the benzene product stream comprises benzene at a concentration of at least 98.00 wt %, based on the total weight of the benzene product stream.

A14. The process of any of the preceding embodiments, wherein the transalkylation conditions comprise a feed inlet temperature of 200° C. to 550° C., a hydrogen to hydrocarbon molar ratio of 1.5 to 10, and an absolute pressure of 380 kPa to 4240 kPa.

A15. The process of any of the preceding embodiments, wherein the transalkylation catalyst comprises a zeolite and a hydrogenation component.

A16. The process of A15, wherein the zeolite is selected from zeolites of the following framework type: FAU, MFI, MOR, MWW, and mixtures and combinations thereof, and the hydrogenation component is selected from iron, cobalt, nickel, palladium, platinum, rhenium, ruthenium, rhodium, iridium, and mixtures and combinations thereof.

A17. The process of any of the preceding embodiments A13 to A16, wherein the benzene purity of the benzene product stream after ceasing introducing sulfolane into the transalkylation reactor at the end of the first period of time is higher than a benzene product stream in a comparative process where sulfolane is not introduced into the transalkylation reactor in the first period of time.

A18. The process of any of the preceding embodiments, wherein the at least one of benzene and toluene is produced by a solvent extraction process using sulfolane as an extraction solvent.

A19. The process of A18, wherein at least a portion of the sulfolane is entrained in the at least one of benzene and toluene and is derived from the solvent extraction process.

A20. The process of any of the preceding embodiments, wherein at least a portion of the sulfolane is introduced into the transalkylation reactor separately from the C9+ aromatic feed and the at least one of benzene and toluene.

B1. A transalkylation process comprising:
feeding a C9+ aromatic feed, molecular hydrogen ($H_2$), sulfolane and at least one of benzene and toluene into a transalkylation reactor having a transalkylation catalyst comprising a metal disposed therein, where the sulfolane is fed at a quantity from 50 ppm to 400 ppm, based on the total weight of the C9+ aromatic feed, the at least one of benzene and toluene;
contacting the C9+ aromatic feed, the at least one of benzene and toluene, the molecular hydrogen, and the sulfolane with the transalkylation catalyst for a first period of time under transalkylation conditions to produce a product mixture rich in xylenes, wherein the transalkylation conditions comprise a feed inlet temperature from 200° C. to 550° C., a hydrogen to hydrocarbon molar ratio from 1.5 to 10, and an absolute pressure from 380 kPa to 4240 kPa; and
ceasing feeding the sulfolane to the transalkylation reactor at the end of the first period;
supplying at least a portion of the product mixture to a benzene distillation column; and
obtaining a benzene product stream from the benzene distillation column.

B2. The process of B1, wherein the first period of time is from 1 to 14 days.

B3. The process of B1 or B2, wherein the first period of time is from 3 to 6 days.

B4. The process of any of the preceding embodiments B1 to B3, wherein the first period of time begins in proximity to a start of a catalyst cycle of the transalkylation catalyst.

B5. The process of any of the preceding embodiments B1 to B4, wherein the sulfolane is fed into the transalkylation unit at a quantity from 70 ppm to 200 ppm, based on the total weight of the C9+ aromatic feed, the sulfolane, and the at least one of benzene and toluene.

B6. The process of any of the preceding embodiments B1 to B5, wherein the transalkylation catalyst comprises a zeolite selected from the following framework types: CHA, EMT, ERI, EUO, FAU, FER, HEU, KFI, LEV, LTA, MAZ, MEI, MEL, MFI, MTT, MTW, MWW, TON, and mixtures and combinations thereof, and a hydrogenation component selected from palladium, platinum, rhenium, and mixtures and combinations thereof.

B7. The process of any of the preceding embodiments B1 to B6, wherein the at least one of benzene and toluene is toluene.

B8. The process of any of the preceding embodiments B1 to B7, wherein the at least of one of benzene and toluene is benzene.

B9. The process of any of the preceding embodiments B1 to B8, wherein the at least one of benzene and toluene is a mixture of benzene and toluene.

B10. The process of any of the preceding embodiments B1 to B9, wherein the benzene product stream comprises benzene at a concentration of at least 99.00 wt %.

B11. The process of any of the preceding embodiments B1 to B10, wherein the benzene purity of the benzene product stream after ceasing introducing sulfolane into the transalkylation reactor at the end of the first period of time is higher than a benzene product stream in a comparative process where sulfolane is not introduced into the transalkylation reactor in the first period of time.

B12. The process of any of the preceding embodiments B1 to B11, wherein the at least one of benzene and toluene is produced by a solvent extraction process using sulfolane as an extraction solvent.

B13. The process of B12, wherein at least a portion of the sulfolane is entrained in the at least one of benzene and toluene and is derived from the solvent extraction process.

B14. The process of any of the preceding embodiments, wherein at least a portion of the sulfolane is introduced into the transalkylation reactor separately from the C9+ aromatic feed and the at least one of benzene and toluene.

What is claimed is:

1. A transalkylation process comprising:
   introducing a C9+ aromatic feed, sulfolane, molecular hydrogen ($H_2$), and at least one of benzene and toluene into a transalkylation reactor having a transalkylation catalyst disposed therein, wherein at least a portion of the sulfolane is (i) introduced into the transalkylation reactor separately from the C9+ aromatic feed and the at least one of benzene and toluene and/or (ii) added into the C9+ aromatic feed and/or the at least one of benzene and toluene; and
   contacting the C9+ aromatic feed, the sulfolane, and the at least one of benzene and toluene with the transalkylation catalyst for a first period of time under transalkylation conditions to produce a product mixture.

2. The process of claim 1, wherein the first period of time is 1 day to 14 days.

3. The process of claim 1, wherein the first period of time begins in proximity to a start of a catalyst cycle of the transalkylation catalyst.

4. The process of claim 1, further comprising ceasing introducing sulfolane into the transalkylation reactor at the end of the first period of time.

5. The process of claim 4, wherein the process further comprises:
   supplying at least a portion of the product mixture into a distillation column without intermediate solvent extraction; and
   obtaining a benzene product stream from the distillation column;
   wherein the benzene product stream after ceasing introducing sulfolane into the transalkylation reactor at the end of the first period of time has a higher benzene purity is higher than a benzene product stream in a comparative process where sulfolane is not introduced into the transalkylation reactor in the first period of time.

6. The process of claim 1, wherein the sulfolane is introduced into the transalkylation reactor at a quantity of 50 ppm to 400 ppm, based on the total weight of the C9+ aromatic feed, the sulfolane, and the at least one of benzene and toluene.

7. The process of claim 1, wherein the sulfolane is fed into the transalkylation reactor at a quantity of 70 ppm to 200 ppm, based on the total weight of the C9+ aromatic feed, the sulfolane, and the at least one of benzene and toluene.

8. The process of claim 1, wherein the C9+ aromatic feed consists essentially of C9+ aromatic hydrocarbons.

9. The process of claim 1, wherein the at least one of benzene and toluene is toluene.

10. The process of claim 1, further comprising:
    supplying at least a portion of the product mixture into a distillation column without intermediate solvent extraction; and
    obtaining a benzene product stream from the distillation column.

11. The process of claim 10, wherein the benzene product stream comprises benzene at a concentration of at least 98.00 wt %, based on the total weight of the benzene product stream.

12. The process of claim 1, wherein the transalkylation conditions comprise a feed inlet temperature of 200° C. to 550° C., a hydrogen to hydrocarbon molar ratio of 1.5 to 10, and an absolute pressure of 380 kPa to 4240 kPa.

13. The process of claim 1, wherein the at least one of benzene and toluene is produced by a solvent extraction process using sulfolane as an extraction solvent.

14. The process of claim 13, wherein at least a portion of the sulfolane is entrained in the at least one of benzene and toluene and is derived from the solvent extraction process.

15. The process of claim 1, wherein at least a portion of the sulfolane is introduced into the transalkylation reactor separately from the C9+ aromatic feed and the at least one of benzene and toluene.

16. The process of claim 1, wherein at least a portion of the sulfolane is added into the C9+ aromatic feed and/or the at least one of benzene and toluene.

17. A transalkylation process, the process comprising:
    feeding a C9+ aromatic feed, molecular hydrogen ($H_2$), sulfolane and at least one of benzene and toluene into a transalkylation reactor having a transalkylation catalyst comprising a metal disposed therein, where the sulfolane is fed at a quantity from 50 ppm to 400 ppm, based on the total weight of the C9+ aromatic feed, the at least one of benzene and toluene, wherein at least a portion of the sulfolane is (i) introduced into the transalkylation reactor separately from the C9+ aromatic feed and the at least one of benzene and toluene and/or (ii) added into the C9+ aromatic feed and/or the at least one of benzene and toluene;
    contacting the C9+ aromatic feed, the at least one of benzene and toluene, the molecular hydrogen, and the sulfolane with the transalkylation catalyst for a first period of time under transalkylation conditions to produce a product mixture rich in xylenes, wherein the transalkylation conditions comprise a feed inlet temperature from 200° C. to 550° C., a hydrogen to hydrocarbon molar ratio from 1.5 to 10, and an absolute pressure from 380 kPa to 4240 kPa; and
    ceasing feeding the sulfolane to the transalkylation reactor at the end of the first period;

supplying at least a portion of the product mixture to a benzene distillation column without an intermediate solvent extraction process; and obtaining a benzene product stream from the benzene distillation column.

18. The process of claim 17, wherein the first period of time is from 1 to 14 days.

19. The process of claim 17, wherein the first period of time begins in proximity to a start of a catalyst cycle of the transalkylation catalyst.

20. The process of claim 17, wherein the sulfolane is fed into the transalkylation unit at a quantity from 70 ppm to 200 ppm, based on the total weight of the C9+ aromatic feed, the sulfolane, and the at least one of benzene and toluene.

21. The process of claim 17, wherein the at least one of benzene and toluene is toluene.

22. The process of claim 17, wherein the benzene product stream comprises benzene at a concentration of at least 99.00 wt %.

23. The process of claim 17, the benzene purity of the benzene product stream after ceasing introducing sulfolane into the transalkylation reactor at the end of the first period of time is higher than a benzene product stream in a comparative process where sulfolane is not introduced into the transalkylation reactor in the first period of time.

24. The process of claim 16, wherein the at least one of benzene and toluene is produced by a solvent extraction process using sulfolane as an extraction solvent.

25. The process of claim 24, wherein at least a portion of the sulfolane is entrained in the at least one of benzene and toluene and is derived from the solvent extraction process.

26. The process of claim 17, wherein at least a portion of the sulfolane is introduced into the transalkylation reactor separately from the C9+ aromatic feed and the at least one of benzene and toluene.

27. The process of claim 17, wherein at least a portion of the sulfolane is added into the C9+ aromatic feed and/or the at least one of benzene and toluene.

* * * * *